US010140711B2

(12) United States Patent
Winternheimer

(10) Patent No.: US 10,140,711 B2
(45) Date of Patent: Nov. 27, 2018

(54) METHOD OF ANALYZING VERTEBRAL EDGES OF VERTEBRAE IN IMAGES ACQUIRED FROM AN UPRIGHT MRI SYSTEM

(71) Applicant: Stella's Practice Management, LLC, Wheaton, IL (US)

(72) Inventor: Jeff Winternheimer, Wheaton, IL (US)

(73) Assignee: Stella's Practice Management, LLC, Wheaton, IL (US)

( * ) Notice: Subject to any disclaimer, the term of this patent is extended or adjusted under 35 U.S.C. 154(b) by 0 days.

(21) Appl. No.: 15/716,210

(22) Filed: Sep. 26, 2017

(65) Prior Publication Data

US 2018/0082422 A1 Mar. 22, 2018

Related U.S. Application Data

(63) Continuation of application No. 15/382,188, filed on Dec. 16, 2016, now Pat. No. 9,773,309, which is a (Continued)

(51) Int. Cl.

| | |
|---|---|
| ***G06K 9/00*** | (2006.01) |
| ***G06T 7/00*** | (2017.01) |
| ***A61B 5/055*** | (2006.01) |
| ***G06K 9/46*** | (2006.01) |
| ***G06K 9/52*** | (2006.01) |

(Continued)

(52) U.S. Cl.

CPC ............ *G06T 7/0012* (2013.01); *A61B 5/055* (2013.01); *A61B 5/107* (2013.01); *A61B 5/407* (2013.01); *G06K 9/4604* (2013.01); *G06K 9/52* (2013.01); *G06T 7/13* (2017.01); *G06T 7/60* (2013.01); *G06T 7/73* (2017.01); *A61B 2576/02* (2013.01); *G06K 2009/4666* (2013.01);

(Continued)

(58) Field of Classification Search

None

See application file for complete search history.

(56) References Cited

U.S. PATENT DOCUMENTS

| | | | |
|---|---|---|---|
| 6,340,363 | B1 | 1/2002 | Bolger et al. |
| 7,123,008 | B1 | 10/2006 | Damadian et al. |

(Continued)

FOREIGN PATENT DOCUMENTS

| | | |
|---|---|---|
| WO | 2007121337 | 10/2007 |
| WO | 2011047197 | 4/2011 |

OTHER PUBLICATIONS

Alyas et al., "Upright positional MRI of the lumbar spine," Clinical Radiology (2008) 63, 1035-1048.

(Continued)

*Primary Examiner* — Tahmina Ansari

(74) *Attorney, Agent, or Firm* — Michael Best & Friedrich, LLP

(57) ABSTRACT

A method of analyzing a spinal region of a subject. The method includes steps of obtaining a first sagittal image of the spinal region of the subject using an upright magnetic resonance imaging unit; identifying a first vertebral edge on a first side of a first disc in the first sagittal image; identifying a second vertebral edge on a second side of the first disc in the first sagittal image; and determining a first angle between the first vertebral edge and the second vertebral edge for the first disc.

20 Claims, 6 Drawing Sheets

Related U.S. Application Data continuation of application No. 14/941,003, filed on Nov. 13, 2015, now Pat. No. 9,524,549, which is a continuation of application No. 13/801,457, filed on Mar. 13, 2013, now Pat. No. 9,218,657.

(60) Provisional application No. 61/658,671, filed on Jun. 12, 2012.

(51) Int. Cl.

| | |
|---|---|
| ***G06T 7/60*** | (2017.01) |
| ***G06T 7/73*** | (2017.01) |
| ***G06T 7/13*** | (2017.01) |
| ***A61B 5/107*** | (2006.01) |
| ***A61B 5/00*** | (2006.01) |

(52) U.S. Cl.
CPC *G06T 2200/04* (2013.01); *G06T 2207/10088* (2013.01); *G06T 2207/30012* (2013.01)

(56) References Cited

U.S. PATENT DOCUMENTS

| | | | | |
|---|---|---|---|---|
| 7,680,525 | B1 * | 3/2010 | Damadian | A61B 5/0555 324/318 |
| 7,835,497 | B2 * | 11/2010 | Haras | A61B 5/1075 378/98 |
| 7,903,851 | B2 | 3/2011 | Reisman et al. | |
| 8,014,575 | B2 | 9/2011 | Weiss et al. | |
| 8,036,730 | B1 | 10/2011 | Damadian et al. | |
| 9,218,657 | B2 * | 12/2015 | Winternheimer | G06T 7/0012 |
| 9,524,549 | B2 | 12/2016 | Winternheimer | |
| 2002/0026192 | A1 * | 2/2002 | Schmiel | A61B 17/1757 606/914 |
| 2004/0236342 | A1 * | 11/2004 | Ferree | A61B 17/025 606/102 |
| 2005/0187459 | A1 | 8/2005 | Trequattrini et al. | |
| 2007/0038070 | A1 | 2/2007 | Tank | |
| 2007/0223799 | A1 * | 9/2007 | Weiss | B60R 25/00 382/131 |
| 2008/0287796 | A1 | 1/2008 | Kiraly et al. | |
| 2009/0240137 | A1 | 9/2009 | Rosa | |
| 2011/0142307 | A1 | 6/2011 | Ghosh et al. | |
| 2013/0329979 | A1 * | 12/2013 | Winternheimer | G06T 7/0012 382/131 |
| 2017/0103530 | A1 * | 4/2017 | Winternheimer | G06T 7/0012 |

OTHER PUBLICATIONS

Beric, “Imaging the spine with upright MRI,” RAD Magazine 36, 422, Jul. 2010, 21-22.

Elsig et al., “Dynamic cervical stenosis revealed by upright functional MRI(fmri),” Eur J Orthop Surg Traumatol (2007) 17:335-336.

Perez et al., “Evaluation of intervertebral disc herniation and hypermobile intersegmental instability in symptomatic adult patients undergoing recumbent and upright MRI of the cervical or lumbosacral spines,” European Journal of Radiology 62 (2007) 444-448.

Siebert et al., “Lumbar spinal stenosis syndrome, diagnostics and treatment,” Nat. Rev. Neurol. 5, 392-403 (2009).

PCT/US2013/045185 International Search Report and Written Opinion dated Sep. 27, 2013 (15 pages).

* cited by examiner

METHOD OF ANALYZING VERTEBRAL EDGES OF VERTEBRAE IN IMAGES ACQUIRED FROM AN UPRIGHT MRI SYSTEM

CROSS-REFERENCE TO RELATED APPLICATIONS

This application is a continuation of U.S. Non-Provisional application Ser. No. 15/382,188, filed Dec. 16, 2016, which is a continuation of U.S. Non-Provisional application Ser. No. 14/941,003, filed Nov. 13, 2015, which is a continuation of U.S. Non-Provisional application Ser. No. 13/801,457, filed Mar. 13, 2013, and which claims the benefit of U.S. Provisional Application No. 61/658,671, filed Jun. 12, 2012, the entire contents of each application is incorporated herein by reference in their entirety.

BACKGROUND OF THE INVENTION

The present invention relates to analysis of data obtained from a subject obtained using a magnetic resonance imaging (MRI), in particular an upright MRI.

Magnetic resonance imaging (MRI) permits imaging of internal structures in a subject's body and is especially useful for studying soft tissues. Among the body structures that can be visualized are the vertebrae, the discs between vertebrae, and related structures. However, when a subject is lying on his or her back, as is the case with conventional MRI devices, the weight and stresses that the vertebrae are normally subjected to are not present and thus the observations and diagnoses are not as accurate as they otherwise could be.

SUMMARY OF THE INVENTION

In one embodiment, the invention provides a method of analyzing a spinal region of a subject. The method includes steps of obtaining a first sagittal image of the spinal region of the subject using an upright magnetic resonance imaging unit; identifying a first vertebral edge on a first side of a first disc in the first sagittal image; identifying a second vertebral edge on a second side of the first disc in the first sagittal image; and determining a first angle between the first vertebral edge and the second vertebral edge for the first disc.

In another embodiment the invention provides a computer-based system for analyzing a spinal region of a subject. The system includes an upright magnetic resonance imaging system, a processor, and a storage medium operably coupled to the processor. The storage medium includes program instructions executable by the processor for generating a sagittal image of a spinal region from data obtained using the upright magnetic resonance imaging system; facilitating identification of a first vertebral edge on a first side of a first disc in the sagittal image; facilitating identification of a second vertebral edge on a second side of the first disc; and determining an angle between the first vertebral edge and the second vertebral edge for the first disc.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

In some embodiments, the invention includes a system 100 for obtaining and analyzing data. The system 100 (FIG. 1) can include an upright magnetic resonance imaging (MRI) unit 110, a controller 120 operatively connected to the MRI unit 110, and one or more computer system 130 operatively connected to the MRI unit 110 to obtain and analyze image data. In various embodiments, the components shown in FIG. 1 may be in one unit or multiple units and some of the elements may be remotely located from others, for example the computer system 130 may be integrated with the MRI unit 110 and controller 120 or may be located at some distance from the MRI unit 110 and/or controller 120, e.g. a short distance away (for example in the same room or building) or much further (e.g. many miles) away. Further, the controller 120 may be integrated with the MRI unit 110 or may be located a short distance or much further away. The controller 120 of the system 100, in various embodiments, may be programmed to carry out one or more steps of the methods described herein, including steps related to data collection, processing, storage, and analysis.

Figure 1:
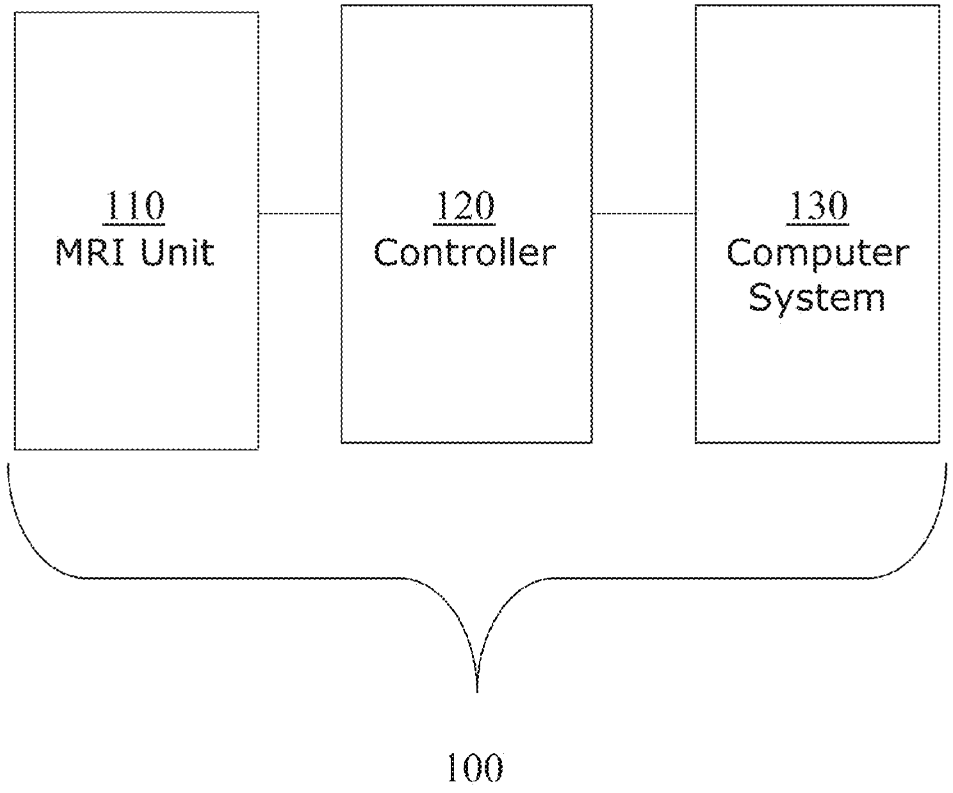
FIG. 1 is a block diagram for a system for obtaining and analyzing data from an upright MRI unit.

The components of the system 100, which may encompass one or more computer system 130, may be in communication with one another through various wired and wireless communication means which may include communications through the Internet (FIG. 1). Each computer system 130 may include an input device, an output device, a storage medium, and a processor. Possible input devices include a keyboard, a computer mouse, a touch screen, and the like. Output devices may include a cathode-ray tube (CRT) computer monitor, a liquid-crystal display (LCD) or LED computer monitor, and the like. Storage media include various types of memory such as a hard disk, RAM, flash memory, and other magnetic, optical, physical, or electronic memory devices. The processor may be any typical computer processor for performing calculations and directing other functions for performing input, output, calculation, and display of data in the disclosed calculator. Implementation of the system 100 includes generating a set of instructions and data that are stored on one or more of the storage media and operated on by a controller. The data associated with the system 100 can include image data and numerical data.

In some embodiments, the system 100 may include a web page for facilitating input, control, analysis, and other functions. In other embodiments, the system 100 may be implemented as a locally-controlled program on a local computer system 130 which may or may not be accessible to other computer systems. In still other embodiments, the system 100 may include modules which provide access to portable devices such as laptops, tablet computers, and smart phones.

In certain embodiments, the invention may include a computer-readable medium, which may include, for example, storage media as described above, where the computer readable medium may include instructions to carry out one or more steps of the methods described herein, including steps related to data collection, processing, storage, and analysis.

In various embodiments, the invention includes a method of analyzing a spinal region of a subject. The subject may be a human or other vertebrate animal, and in various embodiments the subject is a mammal. The subject may have pain, including chronic pain, where the methods of the invention may include identifying one or more structures (e.g. in the subject's spinal column or related anatomical structures) which are abnormal and which might require treatment to alleviate the subject's discomfort and/or restore the structures to a more normal condition.

Figure 2:
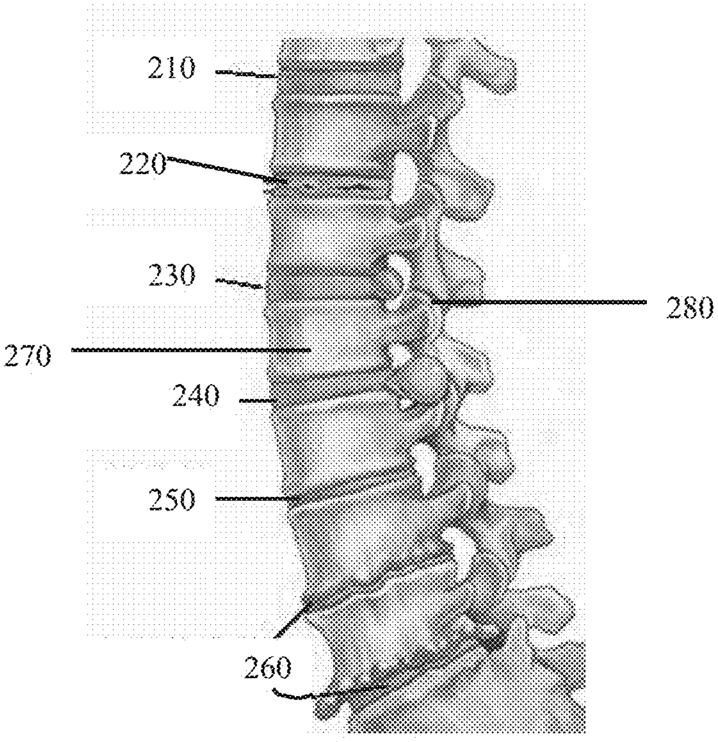
FIG. 2 shows a portion of a spinal column of a human subject.
Figure 3:
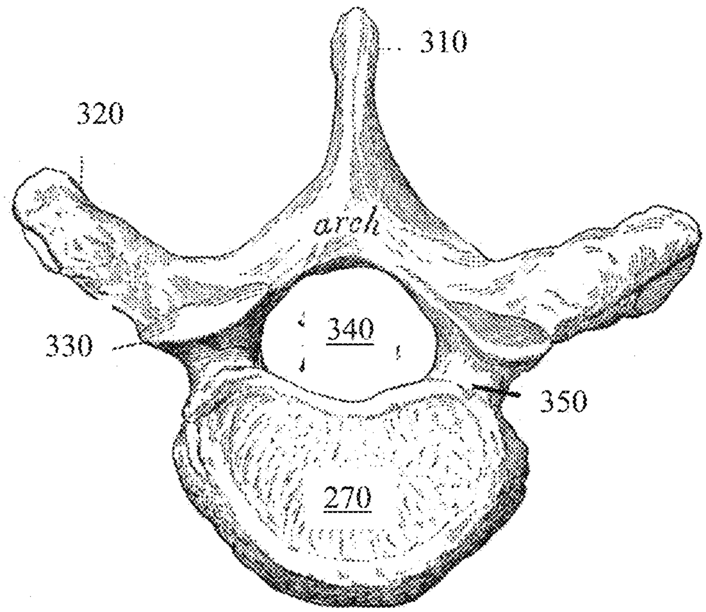
FIG. 3 shows additional anatomical structure of a vertebra.

Among the structures that can be imaged and analyzed according to methods of the invention are shown in FIG. 2, which shows a portion of a spinal column of a human subject including several vertebrae. These structures include a body 270 of a vertebra as well as a facet joint 280 and a normal disc 210. In addition to the normal disc 210, FIG. 2 also depicts several abnormal discs, including a degenerated disc 220, a bulging disc 230, a herniated disc 240, a thinning disc 250, and disc degeneration along with osteophyte formation 260. Additional structures of the vertebrae are shown in FIG. 3, including the spinous process 310, the transverse process 320, the superior articular process 330, the foramen 340, the body 270, and the pedicle 350. The methods can be used to analyze and diagnose conditions from any portion of the spinal column, including vertebrae from the cervical, thoracic, or lumbar regions.

The method includes obtaining a first image of the spinal region of the subject using an upright MRI unit. The use of upright MRI imaging has a distinct unparalleled role in the evaluation and understanding of back pain. An understanding of functional discal alteration is difficult to understand in the normal recumbent posture examination. The weight bearing examination is the most functionally accurate way to understand the vertebral body and discal position in the biped posture. While in general the methods of the invention are performed using an upright MRI, in some embodiments a conventional MRI unit may be used instead. In some embodiments, other medical imaging techniques, including CT scans and conventional x-rays, may be used instead of or in addition to MRI. In various embodiments, one or more contrast agent suitable for the particular imaging method may be used in order to improve visualization of key anatomical structures.

Figure 4:
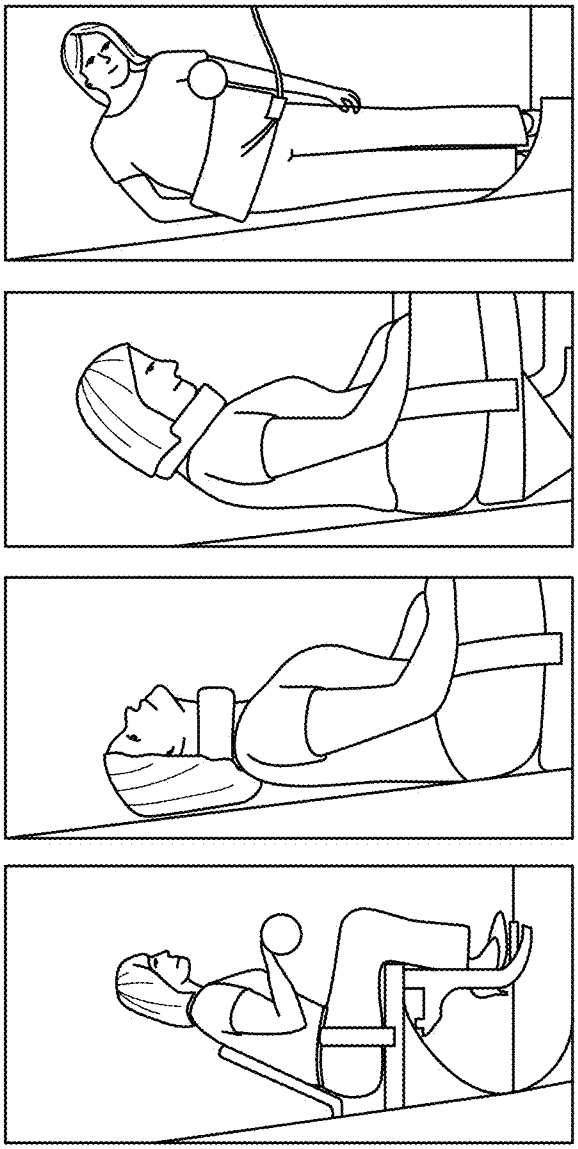
FIG. 4 shows a human subject in various positions in an upright MRI unit.

An upright MRI unit is particularly suitable for the present methods because it permits the subject to stand or sit in an upright or near-upright position during image collection, such that the images of the spinal region show the anatomical structures as they are under their normal weight-bearing stresses (FIG. 4). The subject may be positioned in different ways by the operator (e.g. technician or other medical professional) prior to image collection in order to obtain data from a particular viewpoint. Among the positions that the subject may be placed in (particularly a human subject) are: a standing neutral position (i.e. not bending in any direction); a standing extension position (i.e. bending backward); a standing flexion position (i.e. bending forward); a standing left lateral bending position; a standing right lateral bending position; a standing left rotation position; and a standing right rotation position. Other positions, including seated positions, are also possible.

MRI images are then acquired with the subject in one or more position, generally different positions from one another. The MRI image may include a full volume of data covering some or all of the spinal region of the subject, or the data may be a limited portion such as a slice in a coronal, sagittal, or axial plane. In various embodiments, data from a full volume may be processed to generate one or more views in a coronal (i.e. as viewed from the front of a human subject), sagittal (i.e. as viewed from the side of a human subject), or axial (i.e. as viewed from the top of a human subject) plane, or another plane that is suitable for the particular analysis that is required.

The body 270 of each vertebra has an upper and lower surface that is adjacent to a disc. When viewed from the side (i.e. in a sagittal view), the upper and lower surfaces of each vertebral body 270 appear as edges, where the upper edge of one vertebral body 270 and the lower edge of an adjoining vertebral body 270 define a space in which the disc 210 is located. Measuring the distances and angles between these edges, particularly when measurements are obtained from the subject in several different positions, can be used to identify abnormalities in the subject's spinal column. These abnormalities may in turn be connected with pain or discomfort that the subject is experiencing and might be used to determine treatment to alleviate the pain or discomfort.

In addition to the angles and distances between vertebral bodies 270, image data can also be used to identify the overall condition of the discs 210, in particular to identify one or more possible conditions of the discs such as those shown in FIG. 2 and described above. Additional information regarding the condition of the discs can also be obtained by comparing images obtained when the subject different is in different positions, as the discs may appear normal in one position and abnormal (e.g. bulging) when the subject is in a different position.

Further information that can be obtained from the images can be used to assess the condition of the subject's facet joints 280, for example to identify degeneration, particularly when comparing images that are acquired from the subject in several different positions.

In various embodiments, the angles between adjoining vertebral body 270 surfaces may be carefully measured to determine whether any of the vertebrae are out of alignment with respect to one another. Using a sagittal (side view in the case of a human subject) image, the angle between adjoining vertebral body 270 surfaces can be assessed in an anterior-posterior direction. Similarly, from a coronal (front view in the case of a human subject) image of the subject, the angles between adjoining vertebral body 270 surfaces can be measured to determine the extent to which the surfaces are not aligned. In some embodiments, the angles between adjoining vertebral body 270 surfaces can be measured to within one-tenth of a degree, and the measurement may note how many degrees the surfaces are opened, either in an anterior or a posterior direction. The mensuration of the discs in the sagittal and coronal images for wedging in left/right and the anterior/posterior planes are measured by degrees of opening. This allows small degree of intersegmental disruption to be detected and reevaluated on follow up examination. The mensuration is evaluated without false clinical perception.

Information that can be obtained from either or both of the sagittal or coronal images is the thickness of the disc, which in various embodiments can be measured to within one tenth of a millimeter. Disc volume is also measured by the AP diameter and the width of the disc herniation. This can be evaluated in the neutral and motion examination. Motion studies in flexion/ extension and left and right lateral bending demonstrate information twofold: 1. Changes in the degrees of opening in the anterior/posterior and the left and right lateral bending. This motion can occur within normal expected direction of motion or paradoxical motion. 2. There is also evaluation of disc stability in these excursions which is either stable or unstable in the motion planes. This has been termed "dynamic discal alteration". This can either increase or reduce the prominence of the discal pathology during different excursion.

Using axial (top view in the case of a human subject) images, the condition of the foramen 340 can be evaluated, in particular to see if the foramen 340 is 'patent,' meaning unobstructed.

In one embodiment, the image data obtained from the subject is analyzed using a computer system 130 such as described above (FIGS. 5-6). Information such as thickness and condition of discs, foramen, facet joints, and angles between adjoining vertebral body surfaces may be obtained using automated methods, e.g. using image processing and automated detection of structures and subsequent calculation of data, or manual analysis, or a combination of automated and manual data extraction and analysis. In various embodiments, the information from analyzing one or more views obtained from the subject is used to diagnose the subject and/or plan treatment or select a treatment protocol. The disclosed methods may also be used for follow-up diagnosis of the subject's condition, the results of which may be used to alter the subject's treatment.

Figure 5:
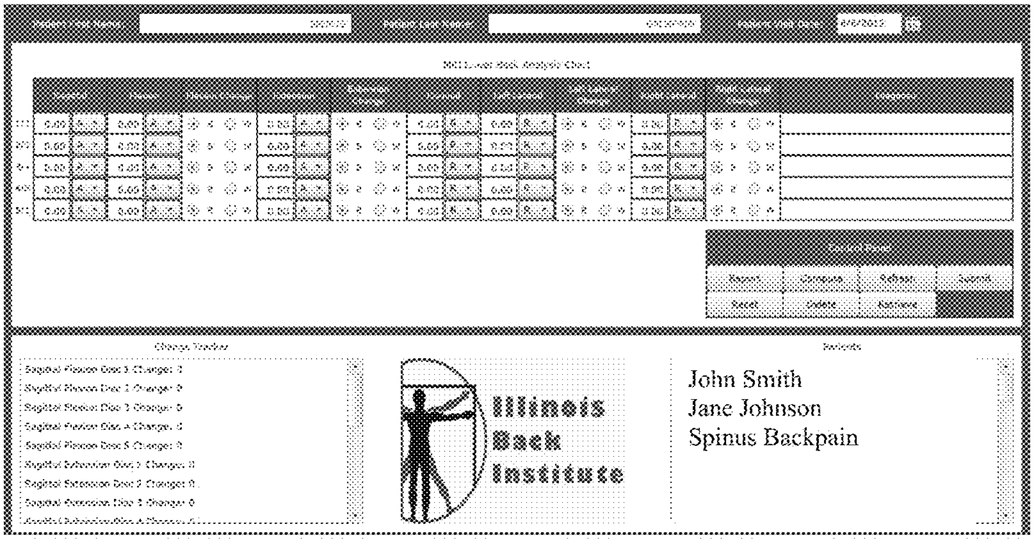
FIG. 5 shows a screen shot of a software system for data collection and analysis.

In one particular embodiment, data obtained from measurements of the subject's discs, e.g. discs in the lumbar or cervical region, are entered into a computer system which then further processes the data and provides information to a clinician or other medical professional. For example, as shown in FIG. 5, data regarding the angles between adjoining vertebral body 270 surfaces for one or more adjacent are entered into a spreadsheet-like interface. The particular discs are identified according to the vertebrae that each is located between, for example '½' indicates the disc found between the L1 and L2 lumbar vertebrae on the Lower Back Analysis Chart shown in FIG. 5. In addition to the angles, also entered is an indication of what direction the angle is facing, such as 'A' for anterior and 'P' for posterior for angles measured in a sagittal view or 'R' for right and 'L' for left in a coronal view.

For a given view (e.g. sagittal, coronal, or axial), image data may be collected and analyzed with the subject in a 'neutral' position (e.g. sitting or standing upright) as well as in a 'bending' position. In various embodiments, the data corresponding to the neutral position is labeled 'sagittal,' 'coronal,' or 'axial.' The respective 'bending' positions are labeled accordingly (e.g. 'flexion' and 'extension' for sagittal views, 'left lateral' and 'right lateral' for coronal views). For each of the bending positions, in some embodiments additional information is obtained and recorded regarding the change in appearance of the corresponding discs, namely whether the appearance is better (marked 'B') or worse (marked 'W') when the patient bends in the given direction. The indication of better or worse may be determined by assessing whether a bulging or herniated disc protrudes outward less (generally considered better) or more (generally considered worse) when the patient bends in the given direction. Finally, an overall diagnosis for the particular disc may be noted in the same row with the other data. In some embodiments, the computer system provides a Change Tracker window which shows the degree of change in the opening of the particular disc as the data is entered, for example the number of degrees of angular change and the direction of the change (e.g. anterior or posterior for sagittal views). Other features that may be provided in other embodiments include a list of patients for whom data is available or for whom new data is to be entered, as well as a control panel including on-screen buttons to select functions including Report, Compute, Refresh, Submit, Reset, Delete, and Retrieve.

Figure 6:
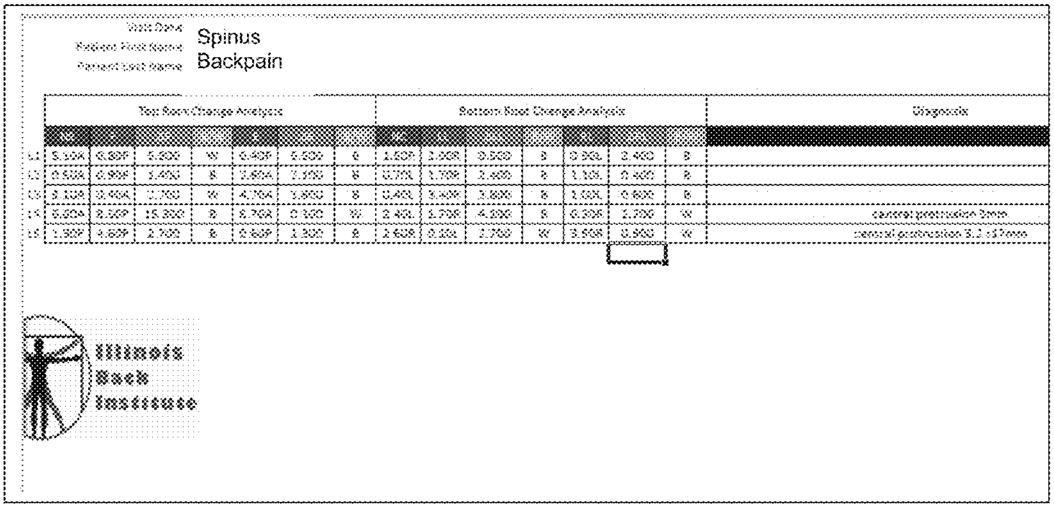
FIG. 6 shows another screen shot of a software system for data collection and analysis.

FIG. 6 shows a screen shot of a data summary report provided in various embodiments of the computer system. In the example shown in FIG. 6, data each for the discs L1-L5 include opening angles for the neutral sagittal (NS) view, flexion (F) view, the change between the neutral and flexion views (ΔF), an indication of whether the condition of the disc (e.g. herniation or bulging) is better (B) or worse (W) upon flexion, as well as comparable data for extension (E), change between the neutral and extension views (ΔE), and an indication of whether the disc appears better or worse upon extension. The data regarding angles also includes an indication of whether the angle is in the anterior (A) or posterior (P) direction.

Similar information may be provided for data obtained in coronal and axial views. FIG. 6 shows data for the neutral coronal (NC) view, left lateral (LL) view, the change between the neutral and left lateral views (ΔLL), right lateral (RL) view, the change between the neutral and right lateral views (ΔRL), and in each case an indication of whether the disc condition is better (B) or worse (W). Finally, a summary chart may include notes concerning a possible diagnosis as well as other information (e.g. measurements of disc protrusions, if any, that are noted).

In other embodiments the computer system includes screens for entering and displaying data corresponding to other regions of the subject's back including the cervical region.

As discussed above, this information is then used by a medical professional to diagnose the subject's condition and, in various embodiments, design a treatment regimen. Similar measurements may be used at various times to assess the effectiveness of the treatment regimen.

Thus, the invention provides, among other things, a method and system for obtaining and analyzing data from an upright Mill from the spinal region of a subject. Various features and advantages of the invention are set forth in the following claims.

What is claimed is:

1. A method of analyzing a spinal region of a subject, the method comprising:

obtaining a first image of the spinal region of the subject using an upright magnetic resonance imaging unit;

identifying a first vertebral edge on a first side of a first vertebra in the first image;

identifying a second vertebral edge on a first side of a second vertebra adjacent to the first vertebra in the first image;

identifying a third vertebral edge on a second side of the second vertebra in the first image;

identifying a fourth vertebral edge on a first side of a third vertebra adjacent the second vertebra in the first image;

determining a first angle between the first vertebral edge and the second vertebral edge;

determining a second angle between the third vertebral edge and the fourth vertebral edge;

determining whether the first vertebra, the second vertebra, and the third vertebra are in alignment based on the first angle and the second angle.

2. The method of claim 1, wherein the first image comprises an image of a lumbar disc between the first vertebral edge and the second vertebral edge.

3. The method of claim 1, wherein the first image comprises an image of a cervical disc between the first vertebral edge and the second vertebral edge.

4. The method of claim 2, further comprising identifying a thickness of the lumbar disc.

5. The method of claim 1, further comprising determining a size of a first disc positioned between the first vertebral edge and the second vertebral edge, wherein determining a first size of the first disc includes identifying a diameter of the first disc.

6. The method of claim 5, further comprising identifying a condition of the first disc, the condition being selected from the group consisting of herniated, thinned, bulging, degenerated, and normal.

7. The method of claim 1, wherein the subject is in a first position when obtaining the first image of the spinal region of the subject using an upright magnetic resonance imaging unit.

8. The method of claim 7, further comprising obtaining a second image of the spinal region of the subject using an upright magnetic resonance imaging unit, wherein the subject is in a second position, different from the first position.

9. The method of claim 1, further comprising identifying a condition of a facet from the first image.

10. The method of claim 1, further comprising obtaining a coronal image.

11. The method of claim 1, further comprising positioning a subject in a position selected from the group consisting of standing neutral, standing extension, standing flexion, standing left lateral bending, standing right lateral bending, standing left rotation, and standing right rotation.

12. The method of claim 1, further comprising diagnosing a spinal pathology based on whether the first vertebra, the second vertebra, and the third vertebra are in alignment.

13. The method of claim 12, further comprising prescribing a treatment protocol for the subject based on the diagnosis.

14. The method of claim 1, wherein at least one step is conducted using a microprocessor.

15. A computer-based system for analyzing a spinal region of a subject, comprising:

an upright magnetic resonance imaging system;

a processor; and a storage medium operably coupled to the processor, wherein the storage medium includes program instructions executable by the processor for generating a first image of a spinal region from data obtained using the upright magnetic resonance imaging system;

facilitating identification of a first vertebral edge on a first side of a first vertebra in the first image;

facilitating identification of a second vertebral edge on a first side of second vertebra in the first image;

facilitating identification of a third vertebral edge on a second side of the second vertebra in the first image;

facilitating identification of a fourth vertebral edge on a first side of a third vertebra in the first image; and determining a first angle between the first vertebral edge and the second vertebral edge;

determining a second angle between the third vertebral edge and the fourth vertebral edge;

determining whether the first vertebra, the second vertebra, and the third vertebra are in alignment based on the first angle and the second angle.

16. The system of claim 15, further comprising determining a size of a first disc positioned between the first vertebral edge and the second vertebral edge, wherein determining a size of the first disc includes identifying a diameter of the first disc.

17. A method of analyzing a spinal region of a subject, the method comprising:

obtaining a series of images of the spinal region of the subject using an upright magnetic resonance imaging unit;

determining a first angle between a first vertebral edge of a first side of a first vertebra and a second vertebral edge of a first side of a second vertebra;

determining a second angle between a third vertebral edge of a second side of the second vertebra and a fourth vertebral edge of a first side of a third vertebra; and determining whether the first vertebra, the second vertebra, and the third vertebra are in alignment based on the first angle and the second angle.

18. The method of claim 17, further comprising diagnosing a spinal pathology based on whether the first vertebra, the second vertebra, and the third vertebra are in alignment.

19. The method of claim 18, further comprising generating a treatment protocol for the subject based on the diagnosis.

20. The method of claim 17, further comprising determining a size of a first vertebral disc positioned between the first vertebral edge and the second vertebral edge, wherein determining a size of the first vertebral disc includes identifying a diameter of the first vertebral disc.

* * * * *